(12) United States Patent
Iwaki et al.

(10) Patent No.: US 11,284,576 B2
(45) Date of Patent: Mar. 29, 2022

(54) HIGH REBAUDIOSIDE C-CONTENT STEVIA PLANT

(71) Applicant: SUNTORY HOLDINGS LIMITED, Osaka (JP)

(72) Inventors: Kazunari Iwaki, Kyoto (JP); Eiichiro Ono, Kyoto (JP); Tadayoshi Hirai, Kyoto (JP); Katsuro Miyagawa, Kyoto (JP)

(73) Assignee: SUNTORY HOLDINGS LIMITED, Osaka (JP)

( * ) Notice: Subject to any disclaimer, the term of this patent is extended or adjusted under 35 U.S.C. 154(b) by 40 days.

(21) Appl. No.: 16/473,094

(22) PCT Filed: Dec. 26, 2017

(86) PCT No.: PCT/JP2017/046805
§ 371 (c)(1),
(2) Date: Oct. 7, 2019

(87) PCT Pub. No.: WO2018/124142
PCT Pub. Date: Jul. 5, 2018

(65) Prior Publication Data
US 2020/0170209 A1      Jun. 4, 2020

(30) Foreign Application Priority Data

Dec. 27, 2016   (JP) .............. JP2016-253543

(51) Int. Cl.
*A01H 6/14*      (2018.01)
*A01H 5/12*      (2018.01)
*A01H 5/10*      (2018.01)

(52) U.S. Cl.
CPC ............. *A01H 6/1488* (2018.05); *A01H 5/10* (2013.01); *A01H 5/12* (2013.01)

(58) Field of Classification Search
None
See application file for complete search history.

(56) References Cited

U.S. PATENT DOCUMENTS

| | | | |
|---|---|---|---|
| PP10,563 P  *    | 8/1998  | Brandie ............... | A01H 6/1488 Plt./373 |
| 8,501,261 B2     | 8/2013  | Markosyan | |
| 2011/0287164 A1  | 11/2011 | Markosyan | |
| 2013/0284164 A1  | 10/2013 | Zhang et al. | |
| 2013/0287894 A1  | 10/2013 | Markosyan | |
| 2017/0290285 A1  | 10/2017 | Wang et al. | |

FOREIGN PATENT DOCUMENTS

| | | |
|---|---|---|
| CN | 103875343 A | 6/2014 |
| EP | 3 611 179 A1 | 2/2020 |
| JP | 2009-517043 A | 4/2009 |
| JP | 2012-504552 A | 2/2012 |
| JP | 2016-515814 A | 6/2016 |
| WO | WO 2007/070224 A2 | 6/2007 |
| WO | WO 2010/038911 A1 | 4/2010 |
| WO | WO 2014/146084 A1 | 9/2014 |
| WO | 2016/049531 A1 | 3/2016 |
| WO | WO 2016/090460 A1 | 6/2016 |

OTHER PUBLICATIONS

ISR issued in PCT/JP2017/046805, dated Apr. 3, 2018 (with English-language translation).
Search Report and Written Opinion issued in Singapore Patent Application No. 11201905914Y, dated Jul. 13, 2020.
Extended European Search Report issued in EP Patent Application No. 17886105.0, dated Sep. 1, 2020.

* cited by examiner

*Primary Examiner* — David H Kruse
(74) *Attorney, Agent, or Firm* — Greenblum & Bernstein, P.L.C.

(57) ABSTRACT

An objective of the present invention is to provide a *Stevia* plant having a high content of rebaudioside C. The present invention provides a high rebaudioside C-content type, non genetically modified *Stevia* plant that has a higher content of rebaudioside C than wild-type *Stevia* varieties, more specifically at least 20% higher content. The present invention further provides: a method for producing such a high rebaudioside C-content type, non genetically modified *Stevia* plant; and dried leaves obtained from such a plant.

16 Claims, No Drawings

Specification includes a Sequence Listing.

HIGH REBAUDIOSIDE C-CONTENT STEVIA PLANT

CROSS REFERENCE TO RELATED APPLICATIONS

The present application is a National Stage of PCT/JP2017/046805, filed Dec. 26, 2017, which application claims priority to Japanese Patent Application No. 2016-253543, filed Dec. 27, 2016.

TECHNICAL FIELD

The present invention relates to a *Stevia* plant with high content of rebaudioside C.

BACKGROUND ART

In response to consumers' diversified needs, various drinks have been developed and are commercially available. Saccharides such as sucrose are components very commonly blended in drinks for the purpose of, for example, conferring sweetness. However, their influence on health due to excessive consumption has been pointed out. Thus, there are growing needs for lower calorie and naturally derived sweeteners. For example, Patent Literature 1 discloses a functional sweetener composition containing a vitamin, a high intensity sweetener, and a sweetness improving composition.

Rebaudioside (hereinafter, also referred to as "Reb") is known as a sweet component contained in a *Stevia* extract. The *Stevia* extract is obtained by extraction and purification from *Stevia* dried leaves. *Stevia* is a perennial plant of the family Compositae with Paraguay in the South America as its place of origin, and its scientific name is *Stevia rebaudiana* Bertoni. *Stevia* contains a component having approximately 300 or more times the sweetness of sugar and is therefore cultivated for use of this sweet component extracted therefrom as a natural sweetener. The presence of various glycosides such as RebA, RebB, RebC, RebD, RebE and RebM has been reported as Reb (JP 2012-504552 A). Among various Rebs, for example, RebA is evaluated as a high intensity sweetener having good quality of sweetness and is widely used. The other Rebs have also been increasingly found to have their unique sweetness and associated taste.

Under these circumstances, a *Stevia* plant containing 3 to 8% by weight of rebaudioside C per dried leaf is known (Patent Literature 3).

CITATION LIST

Patent Literature

Patent Literature 1: JP 2009-517043 A
Patent Literature 2: National Publication of International Patent Application No. 2016-515814
Patent Literature 3: International Publication No. WO 2016/090460 pamphlet

DISCLOSURE OF THE INVENTION

Although a sweet component in these *Stevia* plants offers reasonable sweetness, the problem thereof is larger aftertaste of sweetness as compared with sucrose. To cope with this problem, the present inventors have found that the degree of this aftertaste differs depending on the composition of a *Stevia* extract, and particularly found that rebaudioside C (hereinafter, may be referred to as "RebC") contained in the *Stevia* extract improves the aftertaste of sweetness.

Accordingly, there is a demand for the obtainment of a *Stevia* plant richer in rebaudioside C and the provision of an approach for producing such a plant, a dried leaf obtainable from such a plant, and a food, a drink, etc. containing rebaudioside C obtained from this dried leaf.

The present application provides a high rebaudioside C-content non-genetically modified *Stevia* plant containing rebaudioside C at high content as compared with the wild type *Stevia* species, a method of producing the plant, and a method of screening for the plant.

The present invention enables the obtainment of a *Stevia* plant richer in rebaudioside C and the provision of an approach for producing such a plant, a dried leaf obtainable from such a plant, and a food, a drink, etc. containing rebaudioside C obtained from this dried leaf.

DESCRIPTION OF EMBODIMENTS

Hereinafter, the present invention will be described in detail. The embodiments are given below merely for illustrating the present invention and are not intended to limit the present invention by such embodiments. The present invention can be carried out in various modes without departing from the spirit of the present invention.

1. High Rebaudioside C-Content Non-Genetically Modified *Stevia* Plant of the Present Invention The present invention provides a high rebaudioside C-content non-genetically modified *Stevia* plant comprising rebaudioside C at higher content by 20% or more as compared with the wild type *Stevia* species, wherein the ratio of the content of rebaudioside C to the content of total steviol glycoside is 40% or more (hereinafter, referred to as the "plant of the present invention").

The *Stevia* plant of the present invention is a species derived from a *Stevia* plant of wild species, but a genetic variation which increases the level of rebaudioside C has occurred. The genetic variation occurs in a non-genetically modified manner (mentioned later).

The phrase "comprising rebaudioside C at higher content by 20% or more as compared with the wild type *Stevia* species" means that, when the amount of rebaudioside C contained per unit amount (e.g., 10 ml) of a liquid extract obtained from a fresh leaf (non-dried leaf) of the wild type *Stevia* plant is used as a reference (concentration), the amount (concentration) of rebaudioside C contained per the same unit amount (the same amount as that of the liquid extract obtained from the leaf of the wild type *Stevia* plant) of a liquid extract obtained from a fresh leaf (non-dried leaf) of the *Stevia* plant of the present invention is higher by 20% or more. In this context, the *Stevia* plant of the present invention may comprise rebaudioside C at higher content by 20% or more, 22% or more, 24% or more, 26% or more, 28% or more, 30% or more, 32% or more, 34% or more, 36% or more, 38% or more, 40% or more, 42% or more, 44% or more, 46% or more, 48% or more, 50% or more, 52% or more, 54% or more, 56% or more, 58% or more, 60% or more, 62% or more, 64% or more, 66% or more, 68% or more, or 70% or more as compared with the wild type *Stevia* species.

The phrase "the ratio of the content of rebaudioside C to the content of total steviol glycoside is 40% or more" means that rebaudioside C is present at a ratio of 40% or more to the amount of total steviol glycoside present in a liquid extract obtained from a fresh leaf (non-dried leaf) of the Stevia plant of the present invention. The total steviol glycoside neither includes an unknown steviol glycoside nor includes a steviol glycoside present at a level less than the detection limit. Preferably, the total steviol glycoside is any combination of two or more members selected from the group consisting of rebaudioside A, rebaudioside B, rebaudioside C, rebaudioside D, rebaudioside E, rebaudioside F, rebaudioside I, rebaudioside J, rebaudioside K, rebaudioside N, rebaudioside M, rebaudioside O, rebaudioside Q, rebaudioside R, dulcoside A, rubusoside, steviol, steviolmonoside, steviolbioside and stevioside. In a certain embodiment, the total steviol glycoside may consist of, for example, rebaudioside A, rebaudioside B, rebaudioside C, rebaudioside D, rebaudioside F, rebaudioside M and steviol. In another embodiment, the total steviol glycoside may consist of rebaudioside A, rebaudioside B, rebaudioside C, rebaudioside D, rebaudioside F, rebaudioside M, rebaudioside N, rebaudioside O and steviol.

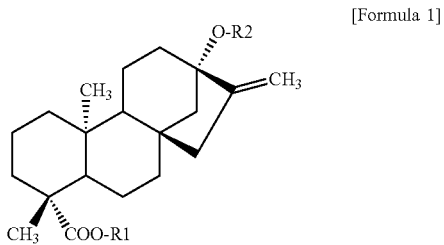

[Formula 1]

| | Compound name | R1 | R2 |
|---|---|---|---|
| 1 | Steviol | H | H |
| 2 | Steviolbioside | H | β-Glc-β-Glc(2→1) |
| 3 | Stevioside | β-Glc | β-Glc-β-Glc(2→1) |
| 4 | Rebaudioside A | β-Glc | β-Glc-β-Glc(2→1)<br>\|<br>β-Glc(3→1) |
| 5 | Rebaudioside B | H | β-Glc-β-Glc(2→1)<br>\|<br>β-Glc(3→1) |
| 6 | Rebaudioside C | β-Glc | β-Glc-α-Rha(2→1)<br>\|<br>β-Glc(3→1) |
| 7 | Rebaudioside D | β-Glc-β-Glc(2→1) | β-Glc-β-Glc(2→1)<br>\|<br>β-Glc(3→1) |
| 8 | Rebaudioside E | β-Glc-β-Glc(2→1) | β-Glc-β-Glc(2→1) |
| 9 | Rebaudioside F | β-Glc | β-Glc-β-Xyl(2→1)<br>\|<br>β-Glc(3→1) |
| 10 | Rubusoside | β-Glc | β-Glc |
| 11 | Dulcoside A | β-Glc | β-Glc-α-Rha(2→1) |
| 12 | Rebaudioside M | β-Glc-β-Glc(2→1)<br>\|<br>β-Glc(3→1) | β-Glc-β-Glc(2→1)<br>\|<br>β-Glc(3→1) |
| 14 | Rebaudioside N | β-Glc-α-Rha(2→1)<br>\|<br>β-Glc(3→1) | β-Glc-β-Glc(2→1)<br>\|<br>β-Glc(3→1) |

Although the content of rebaudioside C in the plant of the present invention is as mentioned above, in the case of obtaining a dried leaf from the plant of the present invention, rebaudioside C may be present in an amount of 7% by weight or more, 8% by weight or more, 9% by weight or more, 10% by weight or more, 11% by weight or more, 12% by weight or more, 13% by weight or more, 14% by weight or more, 15% by weight or more, 16% by weight or more, 17% by weight or more, 18% by weight or more, 19% by weight or more, or 20% by weight or more with respect to the weight of the dried leaf.

In this context, the dried leaf of the plant of the present invention refers to a leaf having a water content decreased to 10% by weight or less, 7% by weight or less, 5% by weight or less, 4% by weight or less, 3% by weight or less, 2% by weight or less, or 1% by weight or less by drying a fresh leaf of the Stevia plant of the present invention. Preferably, the water content of the dried leaf of the plant of the present invention is 3 to 4% by weight.

The plant of the present invention may have at least one of the following properties in addition to the above properties related to rebaudioside C.

(1) The content of rebaudioside A (the amount of rebaudioside A produced) is lower as compared with the wild type Stevia species. More specifically, the content (e.g., the weight concentration in a dried leaf or the like) of rebaudioside A is lower by approximately 40% or more, approximately 50% or more, approximately 60% or more, approximately 70% or more, or approximately 80% or more as compared with the wild type Stevia species.

(2) The content of stevioside (the amount of stevioside produced) is lower as compared with the wild type Stevia species. More specifically, the content (e.g., the weight concentration in a dried leaf or the like) of stevioside is lower by approximately 50% or more, approximately 60% or more, approximately 70% or more, or approximately 80% or more as compared with the wild type Stevia species.

(3) The content of rebaudioside F (the amount of rebaudioside F produced) is higher as compared with the wild type Stevia species. More specifically, the content (e.g., the weight concentration in a dried leaf or the like) of rebaudioside F is higher by approximately 2 times or more, approximately 3 times or more, approximately 4 times or more, approximately 5 times or more, or approximately 6 times or more as compared with the wild type Stevia species.

(4) The ratio of the content of rebaudioside A to the content of total steviol glycoside is lower as compared with the wild type Stevia species. More specifically, the ratio of the content of rebaudioside A to the content of total steviol glycoside (e.g., in a dried leaf or the like) is lower by approximately 8% or more, approximately 20% or more, approximately 30% or more, approximately 40% or more, approximately 50% or more, approximately 60% or more, or approximately 70% or more as compared with the wild type Stevia species.

(5) The ratio of the content of stevioside to the content of total steviol glycoside is lower as compared with the wild type Stevia species. More specifically, the ratio of the content of stevioside to the content of total steviol glycoside (e.g., in a dried leaf or the like) is lower by approximately 30% or more, approximately 40% or more, approximately 50% or more, approximately 60% or more, or approximately 70% or more as compared with the wild type Stevia species.

(6) The ratio of the content of rebaudioside F to the content of total steviol glycoside is higher as compared with the wild type Stevia species. More specifically, the ratio of the content of rebaudioside F to the content of total steviol glycoside (e.g., in a dried leaf or the like) is lower by approximately 3 times or more, approximately 4 times or more, approximately 5 times or more, or approximately 6 times or more as compared with the wild type Stevia species.

The above properties (1) to (6) may be based on the comparison of one specific individual of the plant of the present invention with one specific individual of the wild type *Stevia* species, or may be based on the comparison of an arithmetic mean value from a population consisting of a plurality of individuals of the plant of the present invention with an arithmetic mean value from a population consisting of a plurality of individuals of the wild type *Stevia* species.

In one embodiment, the plant of the present invention has lower contents of rebaudioside A and stevioside (lower amounts of rebaudioside A and stevioside produced) and a higher content of rebaudioside F (a higher amount of rebaudioside F produced) as compared with the wild type *Stevia* species, and/or lower ratios of the contents of rebaudioside A and stevioside to the content of total steviol glycoside and a higher ratio of the content of rebaudioside F to the content of total steviol glycoside as compared with the wild type *Stevia* species, in addition to the above properties related to rebaudioside C.

As mentioned above, the *Stevia* plant of the present invention is a species derived from a *Stevia* plant of wild species, but a genetic variation which increases the level of rebaudioside C has occurred. The genetic variation occurs under natural conditions or by a non-genetic modification approach. The genetic variation is as shown in SEQ ID NO: 1 (hereinafter, referred to as the "genetic polymorphism of the present invention"). The nucleotide sequence of SEQ ID NO: 1 has a single nucleotide polymorphism (SNP; hereinafter, referred to as the "SNP of the present invention") in which the 60th nucleotide of the nucleotide sequence of the corresponding wild type alleles (SEQ ID NO: 2) has varied from wild type A to T.

Thus, the *Stevia* plant of the present invention is characterized by having a polymorphism shown in SEQ ID NO: 1 in the genome. Such a polymorphism has been confirmed in Examples to have statistical correlation with a highly rebaudioside C-containing phenotype.

The *Stevia* plant of the present invention may have the above genetic polymorphism heterozygously or homozygously. In general, a plant having the genetic polymorphism homozygously tends to have higher rebaudioside C content as compared with a plant having the genetic polymorphism heterozygously.

The genetic polymorphism is detectable by PCR method, TaqMan PCR method, sequencing method, microarray method, Invader method, TILLING method, etc., though the detection method is not limited thereto. The detailed method for detecting the genetic polymorphism will be mentioned later.

Examples of the "non-genetic modification approach" herein include a method of inducing a variation in the gene of a host cell (or a host plant) without transfection with a foreign gene. Examples of such a method include a method of allowing a mutagen to act on a plant cell. Examples of such a mutagen include ethyl methanesulfonate (EMS) and sodium azide. For example, the ethyl methanesulfonate (EMS) can be used at a concentration such as 0.1%, 0.2%, 0.3%, 0.4%, 0.5%, 0.6%, 0.7%, 0.8%, 0.9%, or 1.0% to treat a plant cell. The treatment time is 1 to 48 hours, 2 to 36 hours, 3 to 30 hours, 4 to 28 hours, 5 to 26 hours, or 6 to 24 hours. The procedures themselves of the treatment are known in the art and can be performed by dipping a water-absorbed seed obtained through a water absorption process in a treatment solution containing the mutagen at the concentration described above for the treatment time described above.

An alternative example of the non-genetic modification approach can be a method of irradiating a plant cell with radiation or light beam such as X ray, γ ray, or ultraviolet ray. In this case, a cell irradiated using an appropriate dose (ultraviolet lamp intensity, distance, and time) of ultraviolet ray is cultured in a selective medium or the like, and then, a cell, a callus, or a plant having the trait of interest can be selected. In this operation, the irradiation intensity is 0.01 to 100 Gr, 0.03 to 75 Gr, 0.05 to 50 Gr, 0.07 to 25 Gr, 0.09 to 20 Gr, 0.1 to 15 Gr, 0.1 to 10 Gr, 0.5 to 10 Gr, or 1 to 10 Gr. The irradiation distance is 1 cm to 200 m, 5 cm to 100 m, 7 cm to 75 m, 9 cm to 50 m, 10 cm to 30 m, 10 cm to 20 m, or 10 cm to 10 m. The irradiation time is 1 minute to 2 years, 2 minutes to 1 year, 3 minutes to 0.5 years, 4 minutes to 1 month, 5 minutes to 2 weeks, or 10 minutes to 1 week. The irradiation intensity, distance and time differ depending on the type of radiation or the state of the subject to be irradiated (cell, callus, or plant) and can be appropriately adjusted by those skilled in the art.

Approaches such as cell fusion, anther culture (haploid induction), and remote crossing (haploid induction) are also known in the art.

In general, plant cells may involve a mutation during culture. Therefore, it is preferred to regenerate a plant individual, for more stably maintaining the trait.

Although the plant of the present invention is a non-genetically modified *Stevia* plant, the scope of the present invention does not exclude a plant obtained by the ex-post facto genetic recombination with the plant of the present invention as a host (e.g., a plant further provided with another trait by genetic recombination with the plant of the present invention as a host).

The rebaudioside C can be extracted in the state of a liquid extract by reacting a fresh leaf or a dried leaf of the plant of the present invention with a suitable solvent (an aqueous solvent such as water or an organic solvent such as an alcohol, ether or acetone). For the extraction conditions, etc., see a method described in WO 2016/090460, or a method described in Examples mentioned later.

The rebaudioside C can be further purified from the liquid extract thus obtained by use of a method known in the art such as a gradient of ethyl acetate or any of other organic solvents:water, high performance liquid chromatography (HPLC), gas chromatography, time-of-flight mass spectrometry (TOF-MS), or ultra (high) performance liquid chromatography (UPLC).

The rebaudioside C content according to the present invention can be measured by a method described in WO 2016/090460, or a method described in Examples mentioned later. Specifically, a fresh leaf can be sampled from the *Stevia* plant of the present invention, followed by measurement by LC/MS-MS.

The plant of the present invention may include not only the whole plant but a plant organ (e.g., a leaf, a petal, a stem, a root, and a seed), a plant tissue (e.g., epidermis, phloem, soft tissue, xylem, vascular bundle, palisade tissue, and spongy tissue), various forms of plant cells (e.g., suspended cultured cells), a protoplast, a leaf section, a callus, and the like.

The plant of the present invention may also include a tissue culture or a cultured plant cell. This is because the plant can be regenerated by culturing such a tissue culture or a cultured plant cell. Examples of the tissue culture or the cultured plant cell of the plant of the present invention include, but are not limited to, embryos, meristem cells, pollens, leaves, roots, root apices, petals, protoplasts, leaf sections and calluses.

2. Method of Producing Plant of Present Invention

In an alternative aspect, the present invention provides a method of producing a high rebaudioside C-content *Stevia* plant comprising rebaudioside C at higher content by 20% or more as compared with the wild type *Stevia* species, the method comprising a step of crossing the *Stevia* plant of the present invention with a second *Stevia* plant (hereinafter, referred to as the "production method of the present invention").

The "high rebaudioside C-content *Stevia* plant comprising rebaudioside C at higher content by 20% or more as compared with the wild type *Stevia* species" produced by the method has the same phenotype and genetic properties as those of the plant of the present invention.

Specifically, the phenotype of the plant produced by the production method of the present invention is that the plant comprises rebaudioside C at higher content by 20% or more as compared with the wild type *Stevia* species, and the ratio of the content of rebaudioside C to the content of total steviol glycoside is 40% or more. In this context, the phrase "comprising rebaudioside C at higher content by 20% or more as compared with the wild type *Stevia* species" is as mentioned above. The phrase "the ratio of the content of rebaudioside C to the content of total steviol glycoside is 40% or more" is also as mentioned above.

When a dried leaf is obtained from the plant produced by the production method of the present invention, rebaudioside C may be present in an amount of 7% by weight or more, 8% by weight or more, 9% by weight or more, 10% by weight or more, 11% by weight or more, 12% by weight or more, 13% by weight or more, 14% by weight or more, 15% by weight or more, 16% by weight or more, 17% by weight or more, 18% by weight or more, 19% by weight or more, or 20% by weight or more with respect to the weight of the dried leaf. The definition of the dried leaf is as mentioned above.

The genetic properties of the plant produced by the production method of the present invention are to have a genetic polymorphism shown in SEQ ID NO: 1. The plant produced by the production method of the present invention may have the genetic polymorphism heterozygously or homozygously. The method for detecting such a polymorphism is as mentioned above and as mentioned later.

In the production method of the present invention, "hybridizing" means that the plant of the present invention is crossed with a second plant to obtain a progeny plant thereof (plant produced by the production method of the present invention). The hybridizing method is preferably backcross. The "backcross" is an approach of further crossing a progeny plant generated between the plant of the present invention and the second plant, with the plant of the present invention (i.e., a plant having the genetic polymorphism of the present invention) to produce a homozygous plant having the genetic polymorphism of the present invention. When the second plant for use in the production method of the present invention has the same phenotype and genetic properties as those of the plant of the present invention, the crossing is substantially backcross. The genetic polymorphism of the present invention is inheritable according to the Mendel's law. In association with this, the phenotype correlating with the genetic polymorphism, i.e., the high rebaudioside C-content phenotype, is also inheritable according to the Mendel's law.

Alternatively, the plant of the present invention can also be produced by selfing. The selfing can be performed by the self-pollination of the stamen pollen of the plant of the present invention with the pistil of the plant of the present invention.

Since the plant produced by the production method of the present invention has the same phenotype and genetic properties as those of the plant of the present invention, the plant produced by the production method of the present invention can be further crossed with a third *Stevia* plant to produce a high rebaudioside C-content *Stevia* plant comprising rebaudioside C at higher content by 20% or more as compared with the wild type *Stevia* species.

In an alternative embodiment, the plant of the present invention may be produced by regenerating a plant by the culture of the tissue culture or the cultured plant cell mentioned above. The culture conditions are the same as those for culturing a tissue culture or a cultured plant cell of the wild type *Stevia* plant and are known in the art (Protocols for in vitro cultures and secondary metabolite analysis of aromatic and medicinal plants, Method in molecular biology, vo. 1391, pp. 113-123).

3. Method of Screening for Plant of Present Invention

The plant of the present invention or the plant having the same phenotype and genetic properties as those of the plant of the present invention can be screened for by detecting the genetic polymorphism of the present invention from a tissue of this plant. In this context, "screening" means that the plant of the present invention is discriminated from the other plants to select the plant of the present invention.

Thus, in an alternative aspect, the present invention provides a method of screening for a high rebaudioside C-content *Stevia* plant, comprising a step of identifying a polymorphism shown in SEQ ID NO: 1 in the genome of a test plant (hereinafter, may be referred to as the "screening method of the present invention").

Examples of the screening method of the present invention include a method comprising (a) a step of subjecting a genomic or cDNA library of a test *Stevia* plant to amplification treatment and/or hybridization treatment using an oligonucleotide probe comprising a nucleotide sequence having the gene polymorphism of the present invention, and/or an oligonucleotide primer prepared such that, when at least one of the nucleotide sequence of the gene and a complementary sequence thereof is amplified, the amplification fragment comprises the variation site, and (b) a step of detecting the variation site by analyzing the treated product.

Such specific examples of methods of detecting the genetic features of the present invention include, but not limited to, PCR method, TaqMan PCR method, sequencing method, microarray method, Invader method, and TILLING method.

In the case of PCR method, it is preferable to generate a primer such that the 3' end portion has a sequence complementary to the SNP of the present invention. By using a primer designed in this way, the polymerase extension reaction proceeds because the primer hybridizes completely to the template if the template sample has the variation, whereas if the template does not have the SNP of the present invention, the extension reaction does not occur because the nucleotide at the 3' end of the primer mismatches the template. Therefore, PCR amplification is performed using such a primer, and the amplification product is analyzed by agarose gel electrophoresis or the like, and if an amplification product of a predetermined size can be confirmed, the template as the sample has a variation, and if the amplification product is not present, it can be judged that the template does not have a variation.

Alternatively, the genetic polymorphism of the present invention can be detected by designing the primer sequence so that the SNP of the present invention and the primer sequence do not overlap and the genetic polymorphism of the present invention can be PCR amplified, and by sequencing the base sequence of the amplified nucleotide fragment.

For PCR and agarose gel electrophoresis see Sambrook, Fritsch and Maniatis, "Molecular Cloning: A Laboratory Manual" 2nd Edition (1989), Cold Spring Harbor Laboratory Press.

TaqMan PCR method uses fluorescently labeled allele-specific oligos and Taq DNA polymerases (Livak, K. J. Genet). Anal. 14, 143 (1999); Morris T. et al., J. Clin. Microbiol. 34, 2933 (1996)).

The sequencing method is a method of analyzing the presence or absence of a variation by amplifying a region containing the variation by PCR and sequencing the DNA sequence using a Dye Terminator or the like (Sambrook, Fritsch and Maniatis, "Molecular Cloning: A Laboratory Manual" 2nd Edition (1989), Cold Spring Harbor Laboratory Press).

A DNA microarray is one in which one end of a nucleotide probe is immobilized in an array on a support, and includes a DNA chip, a Gene chip, a microchip, a bead array, and the like. By using a probe containing a sequence complementary to the genetic polymorphism of the present invention, the presence or absence of the genetic polymorphism of the present invention can be comprehensively detected. DNA microarray assays such as DNA chips include GeneChip assays (see Affymetrix; U.S. Pat. Nos. 6,045,996; 5,925,525; and 5,858,659). The GeneChip technique utilizes a miniaturized, high density microarray of oligonucleotide probes affixed to a chip.

The invader method combines the hybridization of two reporter probes specific for each allele of a genetic polymorphism such as SNPs and one invader probe to template DNA and the cleavage of DNA by Cleavase enzyme with a special endonuclease activity which cleaves a DNA by recognizing its structure (Livak, K. J. Biomol. Eng. 14, 143-149 (1999); Morris T. et al., J. Clin. Microbiol. 34, 2933 (1996); Lyamichev, V. et al., Science, 260, 778-783 (1993), and the like).

TILLING (Targeting Induced Local Lesions IN Genomes) method is a method in which mutational mismatches in the genomes of a mutagenized mutant population are screened by PCR-amplification and CEL I nuclease-treatment.

4. Extract Derived from Plant of Present Invention and Product Comprising the Extract In a further aspect, the present invention provides a method of producing a rebaudioside C-containing extract, comprising a step of obtaining an extract from the plant of the present invention, or a seed or a dried leaf of the plant (hereinafter, referred to as the "extract production method of the present invention"). The present invention further provides a method of producing rebaudioside C, comprising a step of purifying rebaudioside C from an extract obtained by the extract production method of the present invention (hereinafter, referred to as the "rebaudioside C production method of the present invention").

The extract containing rebaudioside C can be obtained by reacting a fresh leaf or a dried leaf of the plant of the present invention with a suitable solvent (an aqueous solvent such as water or an organic solvent such as an alcohol, ether or acetone). For the extraction conditions, etc., see a method described in WO 2016/090460, or a method described in Examples mentioned later.

The rebaudioside C can be purified from the extract containing rebaudioside C by use of a method known in the art such as a gradient of ethyl acetate or any of other organic solvents:water, high performance liquid chromatography (HPLC), gas chromatography, time-of-flight mass spectrometry (TOF-MS), or ultra (high) performance liquid chromatography (UPLC).

The extract obtained by the extract production method of the present invention (hereinafter, referred to as the "extract of the present invention") is characterized in that the extract comprises rebaudioside C at higher content by 20% or more as compared with the wild type *Stevia* species, and the ratio of the content of rebaudioside C to the content of total steviol glycoside is 40% or more. In this context, the phrase "comprising rebaudioside C at higher content by 20% or more as compared with the wild type *Stevia* species" is as mentioned above. The phrase "the ratio of the content of rebaudioside C to the content of total steviol glycoside is 40% or more" is also as mentioned above. The extract of the present invention differs at least in the ratio of the content of rebaudioside C to the content of total steviol glycoside from an extract similarly obtained by extraction from the wild type *Stevia* species, and is therefore considered to differ in properties such as gustatory properties from the extract similarly obtained by extraction from the wild type *Stevia* species.

The extract of the present invention thus obtained and/or rebaudioside C obtained by the method of producing rebaudioside C according to the present invention can be mixed with other component(s) to produce a novel medicament, flavor or food or beverage with increased content of rebaudioside C. Accordingly, in an alternative aspect, the present invention provides a method of producing a medicament, a flavor or a food or beverage, comprising a step of mixing the extract of the present invention and/or rebaudioside C obtained by the method of producing rebaudioside C according to the present invention with other component(s). The present invention further provides a novel medicament, flavor or food or beverage with increased content of rebaudioside C, obtained by the production method. In this context, the food or beverage means a drink and a food. Thus, in a certain embodiment, the present invention provides a novel medicament, flavor, drink or food and also provides a method of producing the medicament, the flavor, the drink or the food.

Other component(s) is/are not particularly limited as long as the component(s) can be used in a medicament, a flavor or a food or beverage. A natural component and a non-natural component can be used. Examples of the non-natural component include non-naturally occurring compounds, for example, synthetic additives such as synthetic flavoring agents and synthetic preservatives, and fermentation products.

The dosage form of the medicament (pharmaceutical composition) is not particularly limited, and any dosage form such as a solution, a paste, a gel, a solid, or a powder can be adopted. The medicament (pharmaceutical composition) of the present invention can be used in skin external preparations such as oils, lotions, creams, emulsions, gels, shampoos, hair rinses, hair conditioner, enamels, foundations, lipsticks, face powders, facial masks, ointments, powders, dental pastes, aerosols, and cleansing foams as well as bathing agents, hair growth stimulants, skin serums, sun protection agents, and the like. The medicament (pharmaceutical composition) of the present invention may optionally further comprise other pharmaceutically active ingredients (e.g., an anti-inflammatory ingredient) or auxiliary ingredients (e.g., a lubricant ingredient and a carrier ingredient). The pharmaceutically active ingredient or the auxiliary ingredient may be a natural component or a non-natural component.

Examples of the drink include, but are not limited to, fruit juice drinks, soft drinks, sports drinks, tea drinks (e.g., unfermented tea such as green tea, half fermented tea such as oolong tea, fully fermented tea such as black tea, and post-heating fermented tea such as pu-erh tea), fermented drinks (e.g., lactic dinks and alcoholic drinks such as refined sake, wine, beer, and medicated liquors), smoothies, and milk shakes.

The food product includes any processed food product. Examples of the processed food product include, but are not limited to, bread, noodles, pasta, rice, confectionery (cake, ice cream, ice candy, doughnut, baked cookie, candy, hard candy, ices, chewing gum, gummy candy, tablet, snack, rice biscuit, cone cup, and Japanese confectionery such as rice dumpling and steamed bread), tofu (soybean curd) and its processed products, agricultural food products such as canned fruits, fermented food products such as cooking sake, medicated liquors, mirin (sweet cooking sherry), vinegar, soy sauce, miso (bean paste), shiokara (salted fish guts), Vermont vinegar, pickled shallots in sugared vinegar, sweet pickled ginger, lotus roots pickled in vinegar, and Japanese pickles, livestock food products such as yoghurt, ham, bacon, and sausage, seafood products such as kamaboko (minced and steamed fish), ageten (deep fried fish cake), hanpen (puffy fish cake), and shimesaba (vinegared mackerel fillet), soup, potage, jelly, tsukudani (sea foods boiled in soy sauce), dressings, men-tsuyu (soy sauce-based seasoning liquid for noodle), sauce for tempura, sauce for kabayaki eel, sauce for cold noodle, broiled grilled meat sauce, sauces, toothpaste, satsuma-age (fried fish cake), dashi-maki (rolled omelet), sauce for pan-fried noodle, fish jelly products, seasoned laver, tenkasu (crunchy bits of tempura), and furikake (rice seasoning). In one embodiment, the processed food product may be produced from a natural matter as a raw material, but differs in its properties (e.g., physical properties such as elasticity, viscosity, and hardness, and sensory properties such as taste, smell, and texture) from the natural matter. In another embodiment, the processed food product comprises a non-natural component.

Examples

Hereinafter, the present invention will be described with reference to Experimental Examples, Examples, etc. However, the present invention is not limited by these specific embodiments.

(1) Isolation of Line with High RebC Content (M0 Generation)

Approximately 2000 (based on weight) wild type *Stevia* seeds (commercial cultivar in Thailand; introduced in August 2014) were divided into 3 groups, each of which was genetically modified by treatment with 0.1%, 0.2% or 0.3% ethylene methanesulfonate (EMS).

The seeds thus treated with EMS and untreated seeds were seeded in a greenhouse within the Suntory research center to obtain EMS-treated generation (M0 generation) seedlings and untreated seedlings. No difference in the rate of germination was seen among the treatment concentrations.

An appropriate amount of fresh leaves was sampled from the EMS-treated generation (M0 generation) and untreated individuals, and the concentration of each steviol glycoside was quantified by LC/MS-MS (Shimadzu LCMS8050). Specifically, 0.25 g of fresh leaves was dried by freeze drying, and 0.05 g of homogenized dry matter thereof was added into pure water. Extraction by ultrasonic treatment for 20 minutes, and centrifugation and filtration were performed to obtain 0.33 ml of a liquid extract. As a result of analyzing this liquid extract by LC/MS-MS in a LCMS8050 ion mode (Shimadzu LCMS8050), analysis results given below were obtained. The analysis results are shown in tables below (Tables 1-1 and 1-2). In the tables, the number following EM represents a treatment concentration (i.e., EM1=0.1% treatment).

As a result of screening each plant, a plurality of RebC-containing lines (lines with high RebC content) were obtained in which the concentration of rebaudioside C (RebC) in a dried leaf was 5.68 to 9.96% by weight, and the ratio of the content of rebaudioside C to the content of total steviol glycoside was 40% or more. The amount of RebA produced was decreased in common in these lines with high RebC content ("STV" in the tables represents stevioside).

[Weight Concentration in Dried Leaf]

TABLE 1-1

| Line No. | Concentration in dried leaf (%) | | | | |
|---|---|---|---|---|---|
| | RebA | RebC | Stevioside | RebF | Total |
| Line with high RebC content | | | | | |
| EM2-14 | 2.69 | 7.83 | 2.11 | 1.32 | 13.99 |
| EM2-11 | 2.06 | 5.68 | 1.70 | 1.00 | 10.47 |
| EM2-16 | 4.98 | 8.66 | 2.10 | 1.57 | 17.35 |
| EM3-4 | 9.29 | 9.96 | 1.73 | 1.81 | 22.95 |
| Untreated line | | | | | |
| EM0-12 | 10.37 | 1.17 | 8.29 | 0.38 | 20.4 |
| EM0-2 | 13.79 | 1.26 | 5.07 | 0.38 | 20.78 |
| EM0-3 | 8.39 | 1.08 | 9.01 | 0.28 | 19.0 |

[Ratio to Content of Total Steviol Glycoside]

TABLE 1-2

| Line No. | Ratio to amount of total steviol glycoside (%) | | | |
|---|---|---|---|---|
| | RebA | RebC | Stevioside | RebF |
| Line with high RebC content | | | | |
| EM2-14 | 19.2 | 56.0 | 15.1 | 9.47 |
| EM2-11 | 19.7 | 54.3 | 16.2 | 9.55 |
| EM2-16 | 28.7 | 49.9 | 12.1 | 9.06 |
| EM3-4 | 40.5 | 43.4 | 7.5 | 7.90 |
| Untreated line | | | | |
| EM0-12 | 51.0 | 5.75 | 40.7 | 1.9 |
| EM0-2 | 66.39 | 6.05 | 24.38 | 1.85 |
| EM0-3 | 44.3 | 5.68 | 47.5 | 1.5 |

(2) Isolation of Individual of Line with High RebC Content (M1 Generation)

The first treated generation (M1 generation) seeds were produced by the selfing of all the M0 generation individuals. A total of 115 populations was prepared from the 3 types of EMS-treated generation individuals.

The M1 generation seeds were seeded in a greenhouse within the Suntory research center to obtain M1 generation seedlings. An appropriate amount of fresh leaves was sampled from the M1 generation individuals, and the concentration of each steviol glycoside was quantified by LC/MS-MS (Shimadzu LCMS8050).

Specifically, 0.25 g of fresh leaves was dried by freeze drying, and 0.05 g of homogenized dry matter thereof was added into pure water. Extraction by ultrasonic treatment for 20 minutes, and centrifugation and filtration were performed to obtain 0.33 ml of a liquid extract. As a result of analyzing this liquid extract by LC/MS-MS in a LCMS8050 ion mode (Shimadzu LCMS8050), analysis results given below were obtained (Tables 2-1 and 2-2).

In the tables, the number following EM represents a treatment concentration (i.e., EM1=0.1% treatment).

A plurality of individuals with high RebC content were selected on the basis of the analysis results.

Line with High RebC Content
[Weight Concentration in Dried Leaf]

TABLE 2-1

| | Concentration in dried leaf (%) | | | | |
|---|---|---|---|---|---|
| Line No. | RebA | RebC | STV | RebF | Total TSG |
| EM3-45-1 | 0.75 | 14.40 | 0.20 | 3.25 | 18.62 |
| EM2-15-47 | 0.33 | 1.82 | 0.71 | 0.37 | 3.24 |
| EM2-15-33 | 0.27 | 1.24 | 0.46 | 0.22 | 2.19 |
| EM2-15-55 | 0.68 | 1.91 | 0.51 | 0.35 | 3.45 |
| EM2-15-46 | 0.37 | 1.13 | 0.31 | 0.24 | 2.04 |
| EM2-15-35 | 0.29 | 0.93 | 0.31 | 0.16 | 1.68 |
| EM3-16-24 | 2.11 | 6.26 | 2.31 | 1.06 | 11.75 |
| EM2-15-41 | 0.60 | 1.66 | 0.51 | 0.34 | 3.12 |
| EM2-15-6 | 0.74 | 1.92 | 0.59 | 0.36 | 3.61 |
| EM2-15-37 | 0.34 | 1.30 | 0.60 | 0.26 | 2.49 |
| EM2-15-61 | 0.42 | 1.28 | 0.48 | 0.30 | 2.48 |
| EM2-11-87 | 0.51 | 2.65 | 1.52 | 0.45 | 5.13 |
| EM2-15-7 | 0.56 | 1.32 | 0.41 | 0.27 | 2.56 |
| EM2-11-14 | 0.87 | 3.64 | 2.44 | 0.66 | 7.62 |
| EM2-14-11 | 2.55 | 6.62 | 3.70 | 1.05 | 13.95 |
| EM2-14-18 | 1.77 | 5.56 | 3.56 | 0.88 | 11.78 |
| EM2-14-30 | 2.84 | 6.97 | 4.23 | 1.21 | 15.27 |
| EM2-12-48 | 5.03 | 14.75 | 10.42 | 2.15 | 32.44 |
| EM2-3-24 | 5.95 | 8.63 | 3.29 | 1.96 | 19.90 |
| EM2-3-1 | 7.26 | 8.84 | 3.30 | 1.84 | 21.35 |
| EM2-19-12 | 9.51 | 13.87 | 8.37 | 2.71 | 34.52 |
| EM2-10-2 | 5.86 | 5.43 | 2.22 | 1.27 | 14.90 |

[Ratio to Content of Total Steviol Glycoside]

TABLE 2-2

| | Ratio to content of TSG (%) | | | | |
|---|---|---|---|---|---|
| Line No. | RebA | RebC | STV | RebF | Total |
| EM3-45-1 | 4.00 | 77.33 | 1.09 | 17.46 | 100.00 |
| EM2-15-47 | 10.26 | 56.36 | 21.88 | 11.42 | 100.00 |
| EM2-15-33 | 12.50 | 56.31 | 20.93 | 10.19 | 100.00 |
| EM2-15-55 | 19.58 | 55.44 | 14.82 | 10.05 | 100.00 |
| EM2-15-46 | 18.07 | 55.19 | 14.95 | 11.62 | 100.00 |
| EM2-15-35 | 17.12 | 54.95 | 18.14 | 9.73 | 100.00 |
| EM3-16-24 | 17.94 | 53.26 | 19.67 | 9.01 | 100.00 |
| EM2-15-41 | 19.40 | 53.22 | 16.48 | 10.79 | 100.00 |
| EM2-15-6 | 20.57 | 53.08 | 16.19 | 10.04 | 100.00 |
| EM2-15-37 | 13.67 | 51.98 | 23.98 | 10.30 | 100.00 |
| EM2-15-61 | 16.85 | 51.71 | 19.42 | 11.90 | 100.00 |
| EM2-11-87 | 9.99 | 51.63 | 29.54 | 8.75 | 100.00 |
| EM2-15-7 | 21.67 | 51.59 | 16.04 | 10.58 | 100.00 |
| EM2-11-14 | 11.36 | 47.75 | 32.05 | 8.60 | 100.00 |
| EM2-14-11 | 18.31 | 47.46 | 26.50 | 7.55 | 100.00 |
| EM2-14-18 | 15.00 | 47.20 | 30.26 | 7.43 | 100.00 |
| EM2-14-30 | 18.62 | 45.61 | 27.68 | 7.94 | 100.00 |
| EM2-12-48 | 15.52 | 45.46 | 32.14 | 6.63 | 100.00 |
| EM2-3-24 | 29.90 | 43.38 | 16.56 | 9.87 | 100.00 |
| EM2-3-1 | 34.02 | 41.41 | 15.46 | 8.62 | 100.00 |
| EM2-19-12 | 27.55 | 40.18 | 24.24 | 7.86 | 100.00 |
| EM2-10-2 | 39.32 | 36.43 | 14.88 | 8.55 | 100.00 |

Line with Low RebC Content or with Normal RebC Concentration
[Weight Concentration in Dried Leaf]

TABLE 3-1

| | Concentration in dried leaf (%) | | | | |
|---|---|---|---|---|---|
| Line No. | RebA | RebC | STV | RebF | Total TSG |
| EM2-4-13 | 0.00 | 0.00 | 15.14 | 0.00 | 15.14 |
| EM2-8-92 | 0.00 | 0.00 | 4.63 | 0.00 | 4.63 |
| EM2-4-4 | 0.00 | 0.00 | 15.91 | 0.00 | 15.92 |
| EM2-4-17 | 0.02 | 0.00 | 17.48 | 0.00 | 17.50 |
| EM2-4-48 | 0.02 | 0.00 | 15.47 | 0.00 | 15.49 |
| EM2-8-93 | 0.00 | 0.00 | 4.66 | 0.00 | 4.67 |
| EM2-8-84 | 0.02 | 0.00 | 8.05 | 0.00 | 8.06 |
| EM2-4-9 | 0.05 | 0.01 | 18.90 | 0.00 | 18.96 |
| EM1-6-30 | 0.88 | 0.13 | 4.49 | 0.04 | 6.34 |
| EM1-6-19 | 0.76 | 0.08 | 1.25 | 0.02 | 2.81 |
| EM2-11-7 | 0.80 | 0.39 | 12.21 | 0.04 | 13.47 |
| EM2-11-66 | 0.79 | 0.43 | 13.09 | 0.06 | 14.39 |
| EM3-3-5 | 1.66 | 0.13 | 1.67 | 0.05 | 4.02 |
| EM3-3-10 | 3.08 | 0.20 | 1.90 | 0.08 | 5.87 |
| EM1-23-53 | 2.15 | 0.11 | 0.40 | 0.05 | 3.12 |
| EM2-14-7 | 2.19 | 0.12 | 0.68 | 0.05 | 3.38 |
| EM2-14-43 | 3.07 | 0.18 | 0.93 | 0.07 | 4.63 |
| EM1-23-50 | 0.95 | 0.06 | 0.45 | 0.03 | 1.65 |
| EM2-14-57 | 1.74 | 0.10 | 0.44 | 0.04 | 2.49 |
| EM1-23-38 | 2.24 | 0.14 | 0.66 | 0.06 | 3.54 |
| EM1-23-15 | 3.07 | 0.18 | 0.62 | 0.08 | 4.56 |
| EM2-1-18 | 2.85 | 0.22 | 1.15 | 0.10 | 5.37 |
| EM1-23-31 | 2.09 | 0.14 | 0.81 | 0.06 | 3.46 |
| EM1-23-56 | 1.87 | 0.14 | 1.04 | 0.06 | 3.50 |
| EM2-32-6 | 1.61 | 0.23 | 2.18 | 0.07 | 5.51 |
| EM1-23-46 | 2.61 | 0.20 | 1.23 | 0.08 | 4.71 |
| EM2-2-7 | 7.47 | 0.79 | 8.37 | 0.26 | 17.86 |
| EM3-39-11 | 2.97 | 0.20 | 0.76 | 0.08 | 4.33 |
| EM1-23-62 | 1.35 | 0.08 | 0.14 | 0.03 | 1.74 |
| EM2-27-7 | 7.04 | 0.85 | 9.09 | 0.22 | 18.18 |
| EM3-45-4 | 4.68 | 0.30 | 0.65 | 0.11 | 6.28 |
| EM3-19-41 | 4.92 | 0.59 | 6.17 | 0.16 | 12.46 |
| EM2-14-27 | 18.19 | 1.60 | 11.99 | 0.57 | 33.05 |
| EM2-14-28 | 17.94 | 1.54 | 10.43 | 0.57 | 31.87 |
| EM3-19-16 | 5.94 | 0.75 | 7.61 | 0.23 | 15.31 |
| EM1-20-26 | 11.73 | 1.02 | 7.40 | 0.34 | 20.80 |
| EM2-14-38 | 15.49 | 2.00 | 22.50 | 0.51 | 40.68 |
| EM2-14-37 | 19.19 | 1.74 | 11.96 | 0.61 | 34.70 |
| EM2-14-40 | 19.29 | 1.61 | 9.88 | 0.54 | 32.05 |
| EM2-19-22 | 16.26 | 1.96 | 19.91 | 0.43 | 38.74 |
| EM2-1-49 | 2.45 | 0.29 | 1.87 | 0.09 | 5.69 |
| EM2-9-20 | 10.88 | 2.05 | 25.95 | 0.53 | 39.75 |
| EM2-4-14 | 10.79 | 1.38 | 13.57 | 0.32 | 26.27 |
| EM2-8-26 | 7.07 | 0.62 | 3.72 | 0.19 | 11.70 |
| EM2-14-29 | 12.87 | 2.01 | 22.14 | 0.49 | 37.84 |
| EM2-14-25 | 13.83 | 1.72 | 15.89 | 0.46 | 32.03 |
| EM2-4-5 | 13.55 | 1.31 | 8.99 | 0.30 | 24.28 |
| EM2-27-14 | 8.06 | 1.06 | 8.56 | 0.29 | 19.09 |
| EM2-4-12 | 12.75 | 1.64 | 13.13 | 0.36 | 27.95 |
| EM2-8-82 | 6.19 | 0.60 | 3.17 | 0.13 | 10.22 |
| EM2-27-23 | 10.53 | 1.07 | 5.04 | 0.34 | 18.02 |
| EM2-8-73 | 5.06 | 0.51 | 2.73 | 0.14 | 8.53 |

[Ratio to Content of Steviol Glycoside]

TABLE 3-2

| Line No. | Ratio to content of TSG (%) | | | | |
|---|---|---|---|---|---|
| | RebA | RebC | STV | RebF | Total |
| EM2-4-13 | 0.02 | 0.00 | 99.98 | 0.00 | 100.00 |
| EM2-8-92 | 0.04 | 0.00 | 99.96 | 0.00 | 100.00 |
| EM2-4-4 | 0.02 | 0.00 | 99.98 | 0.00 | 100.00 |
| EM2-4-17 | 0.09 | 0.01 | 99.89 | 0.00 | 100.00 |
| EM2-4-48 | 0.10 | 0.01 | 99.87 | 0.00 | 100.00 |
| EM2-8-93 | 0.10 | 0.01 | 99.88 | 0.00 | 100.00 |
| EM2-8-84 | 0.20 | 0.02 | 99.77 | 0.00 | 100.00 |
| EM2-4-9 | 0.26 | 0.04 | 99.69 | 0.01 | 100.00 |
| EM1-6-30 | 13.82 | 2.01 | 70.76 | 0.65 | 100.00 |
| EM1-6-19 | 26.91 | 2.69 | 44.51 | 0.86 | 100.00 |
| EM2-11-7 | 5.98 | 2.91 | 90.68 | 0.29 | 100.00 |
| EM2-11-66 | 5.49 | 3.01 | 90.97 | 0.40 | 100.00 |
| EM3-3-5 | 41.26 | 3.22 | 41.49 | 1.28 | 100.00 |
| EM3-3-10 | 52.43 | 3.48 | 32.43 | 1.43 | 100.00 |
| EM1-23-53 | 68.93 | 3.63 | 12.99 | 1.69 | 100.00 |
| EM2-14-7 | 64.76 | 3.65 | 20.02 | 1.52 | 100.00 |
| EM2-14-43 | 66.26 | 3.87 | 20.06 | 1.60 | 100.00 |
| EM1-23-50 | 57.77 | 3.87 | 27.07 | 1.60 | 100.00 |
| EM2-14-57 | 69.73 | 3.90 | 17.71 | 1.46 | 100.00 |
| EM1-23-38 | 63.09 | 3.94 | 18.63 | 1.63 | 100.00 |
| EM1-23-15 | 67.21 | 3.95 | 13.48 | 1.77 | 100.00 |
| EM2-1-18 | 53.15 | 4.03 | 21.46 | 1.79 | 100.00 |
| EM1-23-31 | 60.37 | 4.08 | 23.54 | 1.60 | 100.00 |
| EM1-23-56 | 53.48 | 4.09 | 29.84 | 1.61 | 100.00 |
| EM2-32-6 | 29.16 | 4.09 | 39.53 | 1.27 | 100.00 |
| EM1-23-46 | 55.49 | 4.17 | 26.17 | 1.66 | 100.00 |
| EM2-2-7 | 41.82 | 4.45 | 46.85 | 1.48 | 100.00 |
| EM3-39-11 | 68.61 | 4.50 | 17.64 | 1.77 | 100.00 |
| EM1-23-62 | 77.29 | 4.51 | 8.15 | 1.70 | 100.00 |
| EM2-27-7 | 38.71 | 4.67 | 49.98 | 1.22 | 100.00 |
| EM3-45-4 | 74.52 | 4.71 | 10.32 | 1.70 | 100.00 |
| EM3-19-41 | 39.51 | 4.72 | 49.54 | 1.28 | 100.00 |
| EM2-14-27 | 55.05 | 4.83 | 36.29 | 1.72 | 100.00 |
| EM2-14-28 | 56.28 | 4.84 | 32.72 | 1.80 | 100.00 |
| EM3-19-16 | 38.76 | 4.87 | 49.69 | 1.48 | 100.00 |
| EM1-20-26 | 56.38 | 4.90 | 35.59 | 1.62 | 100.00 |
| EM2-14-38 | 38.08 | 4.92 | 55.30 | 1.26 | 100.00 |
| EM2-14-37 | 55.29 | 5.02 | 34.46 | 1.76 | 100.00 |
| EM2-14-40 | 60.18 | 5.03 | 30.84 | 1.67 | 100.00 |
| EM2-19-22 | 41.97 | 5.06 | 51.40 | 1.12 | 100.00 |
| EM2-1-49 | 43.00 | 5.11 | 32.89 | 1.56 | 100.00 |
| EM2-9-20 | 27.38 | 5.15 | 65.29 | 1.34 | 100.00 |
| EM2-4-14 | 41.08 | 5.26 | 51.66 | 1.22 | 100.00 |
| EM2-8-26 | 60.43 | 5.31 | 31.78 | 1.64 | 100.00 |
| EM2-14-29 | 34.01 | 5.32 | 58.51 | 1.29 | 100.00 |
| EM2-14-25 | 43.18 | 5.38 | 49.60 | 1.43 | 100.00 |
| EM2-4-5 | 55.81 | 5.39 | 37.03 | 1.23 | 100.00 |
| EM2-27-14 | 42.21 | 5.53 | 44.81 | 1.49 | 100.00 |
| EM2-4-12 | 45.60 | 5.88 | 46.98 | 1.29 | 100.00 |
| EM2-8-82 | 60.59 | 5.89 | 31.02 | 1.31 | 100.00 |
| EM2-27-23 | 58.46 | 5.91 | 27.94 | 1.91 | 100.00 |
| EM2-8-73 | 59.33 | 5.95 | 32.01 | 1.59 | 100.00 |

(3) Isolation of Individual of Line with High RebC Content (M2 Generation)

RebO and RebN concentrations were further quantified for the lines with high RebC content. The quantification conditions were the same as above. Since RebC, RebO, and RebN intramolecularly have a rhamnose residue in common, it was hypothesized that the same enzyme involved in transglycosylation would influence their content ratios. The test was carried out on the concept that this hypothesis can be supported when the respective concentrations of components are in a proportional relation.

[Weight Concentration in Dried Leaf]

TABLE 4-1

| Phenotype | Line No. | Concentration in dried leaf (%) | | | | | | |
|---|---|---|---|---|---|---|---|---|
| | | RebA | RebC | Stevioside | RebF | RebN | RebO | Total |
| High RebC content | EM3-45-1 | 2.1 | 28.4 | 0.5 | 0.6 | 0.00 | 0.00 | 31.6 |
| High RebC content | EM2-3-24 | 20.4 | 14.1 | 4.0 | 0.4 | 0.03 | 0.00 | 38.9 |
| High RebC content | EM2-14-11 | 16.6 | 17.1 | 15.3 | 0.3 | 0.02 | 0.00 | 49.3 |
| High RebC content | EM3-16-24 | 20.2 | 15.9 | 9.5 | 0.3 | 0.02 | 0.00 | 46.0 |
| High RebC content | EM2-19-12 | 19.1 | 17.2 | 13.5 | 0.3 | 0.02 | 0.00 | 50.2 |
| High RebC content | EM2-14-18 | 20.2 | 20.4 | 19.3 | 0.3 | 0.02 | 0.00 | 60.4 |
| High RebC content | EM2-14-30 | 15.0 | 15.2 | 15.5 | 0.3 | 0.01 | 0.00 | 46.1 |
| High RebC content | EM2-3-1 | 26.1 | 14.8 | 4.6 | 0.3 | 0.05 | 0.00 | 45.9 |
| High RebC content | EM2-12-48 | 13.9 | 14.4 | 18.4 | 0.3 | 0.04 | 0.00 | 47.1 |
| Others | EM2-3-31 | 17.2 | 7.1 | 1.8 | 0.2 | 0.05 | 0.01 | 26.3 |
| Others | EM2-3-26 | 28.5 | 10.8 | 5.2 | 0.3 | 0.07 | 0.01 | 44.9 |
| Others | EM2-2-10 | 35.0 | 11.1 | 4.6 | 0.3 | 0.10 | 0.02 | 51.3 |
| Others | EM2-3-19 | 30.0 | 9.2 | 4.8 | 0.2 | 0.10 | 0.01 | 44.4 |
| Others | EM2-27-1 | 17.2 | 2.6 | 0.6 | 0.1 | 0.08 | 0.03 | 20.7 |
| Others | EM2-27-15 | 19.4 | 1.7 | 1.1 | 0.1 | 0.14 | 0.05 | 22.7 |
| Low RebC content | SR4 | 50.1 | 2.5 | 23.2 | 0.1 | 0.06 | 0.00 | 76.1 |
| Low RebC content | SR19 | 59.0 | 2.1 | 10.0 | 0.1 | 0.18 | 0.05 | 71.7 |
| Low RebC content | SR2-102 | 21.2 | 0.6 | 1.1 | 0.0 | 0.14 | 0.06 | 23.5 |
| Null | EM1-11 | 0.0 | 0.0 | 64.7 | 0.0 | 0.00 | 0.00 | 64.8 |
| Null | EM2-4-4 | 0.0 | 0.0 | 44.7 | 0.0 | 0.00 | 0.00 | 44.7 |
| Null | EM2-4-13 | 0.0 | 0.0 | 30.8 | 0.0 | 0.00 | 0.00 | 30.8 |

[Ratio to Content of Total Steviol Glycoside]

TABLE 4-2

| Phenotype | Line No. | Ratio to content of steviol glycoside (%) | | | | | |
|---|---|---|---|---|---|---|---|
| | | RebA | RebC | Stevioside | RebF | RebN | RebO |
| High RebC content | EM3-45-1 | 6.6 | 89.9 | 1.6 | 1.9 | 0.0 | 0.0 |
| High RebC content | EM2-3-24 | 52.5 | 36.1 | 10.3 | 0.9 | 0.1 | 0.0 |
| High RebC content | EM2-14-11 | 33.6 | 34.7 | 31.1 | 0.6 | 0.0 | 0.0 |
| High RebC content | EM3-16-24 | 43.9 | 34.6 | 20.7 | 0.7 | 0.0 | 0.0 |
| High RebC content | EM2-19-12 | 38.0 | 34.3 | 27.0 | 0.7 | 0.0 | 0.0 |
| High RebC content | EM2-14-18 | 33.5 | 33.8 | 32.1 | 0.6 | 0.0 | 0.0 |
| High RebC content | EM2-14-30 | 32.6 | 33.0 | 33.7 | 0.6 | 0.0 | 0.0 |
| High RebC content | EM2-3-1 | 56.8 | 32.2 | 10.1 | 0.7 | 0.1 | 0.0 |
| High RebC content | EM2-12-48 | 29.5 | 30.6 | 39.1 | 0.5 | 0.1 | 0.0 |
| Others | EM2-3-31 | 65.2 | 27.0 | 6.8 | 0.7 | 0.2 | 0.0 |
| Others | EM2-3-26 | 63.4 | 24.0 | 11.7 | 0.6 | 0.2 | 0.0 |
| Others | EM2-2-10 | 68.2 | 21.7 | 9.1 | 0.5 | 0.2 | 0.0 |
| Others | EM2-3-19 | 67.5 | 20.8 | 10.8 | 0.4 | 0.2 | 0.0 |
| Others | EM2-27-1 | 83.1 | 12.5 | 2.7 | 0.5 | 0.4 | 0.1 |
| Others | EM2-27-15 | 85.6 | 7.5 | 4.7 | 0.3 | 0.6 | 0.2 |
| Low RebC content | SR4 | 65.8 | 3.3 | 30.5 | 0.1 | 0.1 | 0.0 |
| Low RebC content | SR19 | 82.4 | 2.9 | 13.9 | 0.1 | 0.2 | 0.1 |
| Low RebC content | SR2-102 | 90.2 | 2.4 | 4.8 | 0.1 | 0.6 | 0.3 |
| Null | EM1-11 | 0.0 | 0.1 | 99.9 | 0.0 | 0.0 | 0.0 |
| Null | EM2-4-4 | 0.0 | 0.1 | 99.9 | 0.0 | 0.0 | 0.0 |
| Null | EM2-4-13 | 0.0 | 0.0 | 100.0 | 0.0 | 0.0 | 0.0 |

(4) Genetic Polymorphism of High RebC-Content Plant (5) Detection of Genetic Polymorphism Unique to High RebC-Content Plant Genomic DNA was extracted from a *Stevia* leaf desired to be examined for the presence or absence of the genetic polymorphism of the present invention. PCR was performed with the extracted genomic DNA as a template. The PCR reaction solution was prepared using Blend Taq (Toyobo Co., Ltd.) according to the instruction of Blend Taq. The PCR amplification of a DNA fragment was performed using 5'-TGGTCACCCTCTAATCATGCTACCG-3' (SEQ ID NO: 3) as a Fw primer and 5'-TTAACTCTCATGATC-GATGGCAACCGCACGCGCATTCTTTTCCAAC-3' (SEQ ID NO: 4) as a Rv primer. The PCR conditions involved 35 repetitions of 3-step reaction of 95° C. for 2 minutes, 55° C. for 30 seconds, and 72° C. for 30 seconds. The DNA fragment amplified by PCR was cleaved with a restriction enzyme (SpeI; Toyobo Co., Ltd.). An enzymatic reaction solution containing 12 μL of the reaction solution after the PCR, 2 μL of H buffer, 1 μL of SpeI, and 5 μL of pure water was prepared. The enzymatic reaction solution was left standing at 37° C. for 16 hours to perform enzymatic reaction. The enzymatic reaction solution digested with the restriction enzyme was applied to LabChip GX Touch HT (PerkinElmer Inc.). A trace amount of the enzymatic reaction solution was electrophoresed on DNA 5 k/RNA CZE LabChip, and the content of DNA in the mobile phase was detected by UV. A pseudo electrophoretic pattern was prepared to detect markers.

As a result of the detection described above, an upper band than that of the wild type was detected using fragment #8 (1412, A>T) in individuals with very high RebC concentration (EM3-45-1, EM3-16-24, EM2-14-11, EM2-14-18, and EM2-14-30). On the other hand, a band of the same size or a comparable size as that of the wild type was detected homozygously or heterozygously in individuals with the same level of or somewhat higher RebC concentration (EM2-14, EM2-11, EM2-16, EM2-14-38, EM3-19-16, EM2-14-27, EM2-2-7, EM2-32-6, EM1-11, EM2-4-4, and EM2-4-13) as compared with the wild type.

The polynucleotide of each band was analyzed for its nucleotide sequence. The nucleotide sequence (heterozygous) of the band for EM3-16-24, EM2-14-11, EM2-14-18, and EM2-14-30 is shown in SEQ ID NO: 5. The nucleotide sequence (homozygous) of the band for EM-3-45-1 is shown in SEQ ID NO: 6. The nucleotide sequence of the band for EM2-14-38, EM1-11, and EM2-2-4 is shown in SEQ ID NO: 7 (homozygous).

All the stocks having a phenotype of high RebC content had the nucleotide sequence of SEQ ID NO: 1 in common. This sequence had a polymorphism in which the 60th base counted from the 5' end of the corresponding wild type sequence (SEQ ID NO: 2) varied from A to T. As a result of further statistically analyzing the correlation of the phenotype of high RebC concentration with the polymorphism of SEQ ID NO: 1, this polymorphism was found to have statistical correlation with the phenotype of high RebC concentration. Specifically, a segregation ratio in progeny of a line with high RebC content (heterozygous A/T)×a line with low RebC content (wild homozygous A/A) can be predicted to be high RebC content:low RebC content=1:1 on the basis of null hypothesis. The RebC phenotype observation values of 22 individuals of progeny obtained by the test cross were high content:low content=7:15. Therefore, the expected value was high content:low content=11:11. As a result of conducting goodness of fit test on the segregation analysis results, $\chi 2$ was 2.91, and the rejection region at df=1 and $\alpha$=0.05 was 3.84. Therefore, there was no statistically significant difference between the observation value (actual segregation ratio) and the expected value, demonstrating that both of them were fit.

Specifically, as a result of the test cross, the marker test results and the phenotype are in a constant relation because of the 1:1 segregation ratio of high RebC content:low RebC content, revealing that a RebC genotype can be defined by this SNP.

These results revealed that an individual with high RebC concentration is detectable at the genome level by use of this procedure on the presence or absence of the genetic polymorphism of the present invention.

INDUSTRIAL APPLICABILITY

The present invention enables the more efficient provision of rebaudioside C and can therefore provide a medicament, a flavor or a food or beverage, etc. comprising a sufficient amount of rebaudioside C and thereby offering improved aftertaste of sweetness ascribable to *Stevia*.

The invention claimed is:

1. A high rebaudioside C-content non-genetically modified *Stevia* plant comprising a rebaudioside C content of 15% by weight or more in a dried leaf thereof, and comprising the A>T polymorphism at the 60th nucleotide of SEQ ID NO: 1 in the genome.

2. A seed of the plant according to claim 1.

3. A dried leaf of the plant according to claim 1.

4. A tissue culture or a cultured plant cell of the plant according to claim 1, wherein said tissue culture or cultured plant cell comprises said polymorphism.

5. The tissue culture or the cultured plant cell according to claim 4, which is an embryo, a meristem cell, a pollen, a leaf, a root, a root apex, a petal, a protoplast, a leaf section and a callus.

6. A method of producing a high rebaudioside C-content *Stevia* plant comprising a rebaudioside C content of 15% by weight or more in a dried leaf thereof, the method comprising crossing a *Stevia* plant according to claim 1 with a second *Stevia* plant.

7. The method according to claim 6, wherein the second plant is the *Stevia* plant according to claim 1.

8. A method of producing a rebaudioside C-containing extract, comprising obtaining an extract from the plant according to claim 1.

9. A method of producing rebaudioside C, comprising purifying rebaudioside C from the rebaudioside C-containing extract according to claim 8.

10. A method of producing a medicament, a flavor or a food or beverage, comprising mixing the extract obtained by the method according to claim 8 with other component(s).

11. A method of screening for a high rebaudioside C-content *Stevia* plant, comprising identifying the A>T polymorphism at the 60th nucleotide of SEQ ID NO: 1 in the genome of a test plant.

12. The method according to claim 11, further comprising measuring a content of rebaudioside C in a leaf tissue.

13. A method of producing a rebaudioside C-containing extract, comprising obtaining an extract from the dried leaf according to claim 3.

14. A method of producing rebaudioside C, comprising purifying rebaudioside C from the rebaudioside C-containing extract according to claim 13.

15. A method of producing a medicament, a flavor or a food or beverage, comprising mixing the extract obtained by the method according to claim 13 with other component(s).

16. A method of producing a medicament, a flavor or a food or beverage, comprising mixing rebaudioside C obtained by the method according to claim 14 with other component(s).

* * * * *

SEQUENCE LISTING

<160> NUMBER OF SEQ ID NOS: 7

<210> SEQ ID NO 1
<211> LENGTH: 60
<212> TYPE: DNA
<213> ORGANISM: Stevia rebaudiana

<400> SEQUENCE: 1
gagtaaaatc tataacgaca ctaaggtgga aaaagaatat gtaagccaat tcgtagactt    60

<210> SEQ ID NO 2
<211> LENGTH: 60
<212> TYPE: DNA
<213> ORGANISM: Stevia rebaudiana

<400> SEQUENCE: 2
gagtaaaatc tataacgaca ctaaggtgga aaaagaatat gtaagccaat tcgtagacta    60

<210> SEQ ID NO 3
<211> LENGTH: 25
<212> TYPE: DNA
<213> ORGANISM: Artificial Sequence
<220> FEATURE:
<223> OTHER INFORMATION: primer

<400> SEQUENCE: 3
tggtcaccct ctaatcatgc taccg    25

<210> SEQ ID NO 4
<211> LENGTH: 46
<212> TYPE: DNA
<213> ORGANISM: artificial
<220> FEATURE:
<223> OTHER INFORMATION: primer

<400> SEQUENCE: 4
ttaactctca tgatcgatgg caaccgcacg cgcattcttt tccaac    46

<210> SEQ ID NO 5
<211> LENGTH: 258
<212> TYPE: DNA
<213> ORGANISM: Stevia rebaudiana
<220> FEATURE:
<221> NAME/KEY: misc_feature
<222> LOCATION: (258)..(258)
<223> OTHER INFORMATION: The "n" at the position 258 may be "a" or "t".

<400> SEQUENCE: 5
tggtcaccct ctaatcatgc taccgctttt tggggaccaa cctctgaatg ctcgattact    60
ggaggacaaa caggtgggaa tcgagatacc aagaaatgag gaagatggtt gcttgaccaa   120
ggagtcggtt gctagatcac tgaggtccgt tgttgtggaa aacgaagggg agatctacaa   180
ggcgaacgcg agggagctga gtaaaatcta taacgacact aaggtggaaa agaatatgt   240 aagccaattc gtagactn    258

<210> SEQ ID NO 6
<211> LENGTH: 258
<212> TYPE: DNA
<213> ORGANISM: Stevia rebaudiana

<400> SEQUENCE: 6
tggtcaccct ctaatcatgc taccgctttt tggggaccaa cctctgaatg ctcgattact    60
ggaggacaaa caggtgggaa tcgagatacc aagaaatgag gaagatggtt gcttgaccaa   120

```
ggagtcggtt gctagatcac tgaggtccgt tgttgtggaa aacgaagggg agatctacaa      180
ggcgaacgcg agggagctga gtaaaatcta taacgacact aaggtggaaa aagaatatgt      240
aagccaattc gtagactt                                                    258

<210> SEQ ID NO 7
<211> LENGTH: 258
<212> TYPE: DNA
<213> ORGANISM: Stevia rebaudiana

<400> SEQUENCE: 7
tggtcaccct ctaatcatgc taccgctttt tggggaccaa cctctgaatg ctcgattact       60
ggaggacaaa caggtgggaa tcgagatacc aagaaatgag gaagatggtt gcttgaccaa      120
ggagtcggtt gctagatcac tgaggtccgt tgttgtggaa aacgaagggg agatctacaa      180
ggcgaacgcg agggagctga gtaaaatcta taacgacact aaggtggaaa aagaatatgt      240
aagccaattc gtagacta                                                    258
```